US006303130B1

(12) United States Patent
Purdy et al.

(10) Patent No.: US 6,303,130 B1
(45) Date of Patent: Oct. 16, 2001

(54) *PASTEURELLA HAEMOLYTICA* VACCINE INACTIVATED BY ULTRAVIOLET LIGHT

(75) Inventors: Charles W. Purdy, Amarillo; David C. Straus, Lubbock, both of TX (US)

(73) Assignee: The United States of America as represented by the Secretary of Agriculture, Washington, DC (US)

( * ) Notice: Subject to any disclaimer, the term of this patent is extended or adjusted under 35 U.S.C. 154(b) by 0 days.

(21) Appl. No.: 08/151,580

(22) Filed: Nov. 2, 1993

(51) Int. Cl.[7] .................................................. A61K 39/102
(52) U.S. Cl. ..................................... 424/255.1; 424/184.1
(58) Field of Search ............................ 424/88, 92, 184.1, 424/255.1, 184

(56) References Cited

U.S. PATENT DOCUMENTS 2,421,382 * 6/1947 Levinson et al. ...................... 424/78
4,058,599 * 11/1977 Bauer .................................... 424/92

FOREIGN PATENT DOCUMENTS

30775 * 12/1985 (DE) ........................... A61L/39/002
8606312 * 12/1985 (WO) .

OTHER PUBLICATIONS

Jericho et al, Vaccine 8:315–320, 1990.*
Confer et al. Am J. Vet Res 46: 342–347, 1985.*
Purdy et al Am J Vet Res 52: 1214–1220, 1991.*
Purdy et al Am J Vet Res 51:1629–1634, 1990.*
Printout of Database Search Cole et al, Note Progress: 9201 to 9212.*
Confen et al. Am J. Vet Res 46: 342–347, 1985.*
Webster's Ninth New Collegiate Dictionary, p. 262.*
Sonneborn et al Infusions/tien. Klin Ernaltr 5:41–49, 1978 (Abstract Only.*
Lo et al, Mutation Research 263:159–163, 1991.*
Purdy, Charles W., et al., "*Pasteurella haemolytica* ultra–violet irradiated vaccine compared by parenteral and aerosol routes in the goat model", Abstracts of Papers, Presented at the 73rd Annual Meeting of the Conference of Research Workers In Animal Diseases, Nov. 9–10, 1992, p. 43.

Bushueva, N. B., et al., CAB Abstracts, 0624392, 0V057–06825; 0I055–00011; 7A014–00189, Abstract of *Veterinariya*, Moscow, USSR 1987, No. 6:28–30, "Effect of different methods of inactivation on the immunogenicity of *Pasteurella multocida*".

Chai, Y., et al., "A 'Live' Vaccine of Non Replicatable *Pasteurella Multocida* FS3 Cells Prepared by Psoralen Treatment and Long Wave UV Irradiation", *Isreal Journal of Veterinary Medicine*, 44(3):195–201, (1988).

Lo, Reggie Y.C., and MacDonald, Laura E., "*Pasteurella haemolytica* is highly sensitive to ultraviolet irradiation", *Mutation Research*, 263, (1991) 159–163.

Whiteley, L.O., et al., "Alterations in Pulmonary Morphology and Peripheral Coagulation Profiles Caused by Intratracheal Inoculation of Live and Ultraviolet Light–Killed *Pasteurella haemolytica* A1 in Calves", *Vet. Pathol*, 28:275–285 (1991).

Debey, B.M., et al., "A Comparison of the Intratracheal, Intravenous and Intratonsillar Routes of Inoculation of Goats with *Pasteurella haemolytica*" , Veterinary Research Communication, 16 (1992), 247–251.

Purdy, Charles W., et al., "Immune response to pulmonary injection of *Pasteurella haemolytica*—impregnated agar beads followed by transthoracic challenge exposure in goats", *Am. J. Vet. Res.*, vol. 51, No. 10, Oct. 1990, pp. 1629–1639.

* cited by examiner

*Primary Examiner*—Lynette R. F. Smith
*Assistant Examiner*—Ginny Allen Portner
(74) *Attorney, Agent, or Firm*—M. Howard Silverstein; Randall E. Deck; John D. Fado

(57) ABSTRACT

A novel vaccine for immunizing animals against *Pasteurella haemolytica* infection is disclosed. The vaccine is composed of whole killed cells of *P. haemolytica* in a dosage effective to immunize an animal against the organism, in combination with a pharmaceutically acceptable carrier. The killed cells of *P. haemolytica* are produced by irradiating viable cells with ultraviolet light for a sufficient period of time to kill the cells.

18 Claims, 10 Drawing Sheets

PC
NC
Total leukocytes count (X 1000)/mm3
26.5
24.5
22.5
20.5
18.5
16.5
14.5
12.5
10.5

PH1-O
CPS
PH1-I
PH1-I-SC
Total leukocytes count (X 1000)/mm3
26.5
24.5
22.5
20.5
18.5
16.5
14.5
12.5
10.5
O
AG
7
21
AG
34
CH
38
EU
Sampling days PC
NC
Geometric mean anticytotoxin titer
0
5
10
15
20
25
30
35
40

PH1-O
CPS
PH1-I
PH1-I-SC
–21
O
AG
7
14
21
AG
28
34
CH
38
EU
Sampling days

PC
NC
CH50 units / mL serum
130
120
110
100
90
80
70
60
50

PH1-O
CPS
PH1-I
PH-I-SC
CH50 units / mL serum
130
120
110
100
90
80
70
60
50
O
AG
7
14
21
AG
28
34
CH
38
EU
Sampling days

PC
NC

PH1-0
CPS
PH1-I
PH1-I-SC
Geometric mean IHA titer
2100
1680
1260
840
420
200
150
100
50
0
–21
O
AG
7
14
21
AG
28
34
CH
38
EU
Sampling days NC
PC1
PC2
Ph1 IHA titer (geometric mean)
2100
1750
1400
1050
700
400
350
300
250
200
150
100
50
0

PR1
PR2
PR3
PR4
PR5
Ph1 IHA titer (geometric mean)
2100
1750
1400
1050
700
400
350
300
250
200
150
100
50
0
0
AG
7
14
21
AG
28
41
AG
45
Sampling Days Consolidated lesions (cm³)
6
5
4
3
2
1
0
NC
PC
PC2
PR1
PR2
PR3
PR4
PR5
Left Lung Consolidated lesions (cm³)
360
330
300
270
240
210
180
150
120
90
60
30
0
NC
PC
PC2
PR1
PR2
PR3
PR4
PR5
Right Lung

*PASTEURELLA HAEMOLYTICA* VACCINE INACTIVATED BY ULTRAVIOLET LIGHT

BACKGROUND OF THE INVENTION

1. Field of the Invention

This invention relates to a novel vaccine against *Pasteurella haemolytica* which offers superior protection and safety over existing vaccines.

2. Description of the Prior Art

*Pasteurella haemolytica* is a common respiratory pathogen of animals, particularly bovine, sheep, goats, and exotic zoo ruminants. For example, *P. haemolytica* serotype 1 (Ph 1) is involved with most acute fibrinohemorrhagic pneumonias that develop in market stressed feeder/stocker calves after shipment (Lillie, 1974, Can. Vet. J., 15:233–242). While development of a safe and effective vaccine would greatly benefit the cattle industry, prevention of pneumonic pasteurellosis has proven to be quite difficult (Frank and Smith, 1983, Am. J. Vet. Res., 44:981–985; Mosier et al., 1989, Am. J. Vet. Res., 47:1–10). A number of vaccines composed of bacteria and viruses have been examined in recent years for the prevention of this disease. However, most of these vaccines have had little positive effect, and bovine pasteurellosis remains a major concern (Martin, 1983, Can. Vet. J., 24:10–19).

The experimental induction of acute bovine respiratory tract lesions in cattle by *P. haemolytica* alone stimulated a great deal of research examining the use of *P. haemolytica* bacterins as vaccines. In the 1970s and 1980s, three studies produced an experimental fibrinous pneumonia similar to that seen in actual cases of shipping fever (Friend et al., 1977, Can. J. Compar. Med., 41:219–223; Carter, 1973, J. Amer. Vet. Med. Assoc., 163:863–864; Gibbs et al., 1984, Res. Vet. Sci., 37:154–166). Early results employing bacterin vaccines did not look promising. In a study published by Friend in 1977 (Friend et al., 1977, Can. J. Compar. Med., 41:77–83), killed *P. haemolytica* given concomitantly by aerosol and subcutaneous routes produced more severe lesions in vaccinated animals than the controls, following intratracheal *P. haemolytica* challenge. Wilke et al. (1980, Am. J. Vet. Res., 41:1773–1778) observed similar negative effects in studies in which calves were injected subcutaneously with a formalin-killed *P. haemolytica* vaccine. They observed that protection against *P. haemolytica* following intrabronchial challenge with this organism was lowered compared with controls. Perhaps the puzzling results obtained with bacterins stimulated the examination of live vaccines for prevention of pneumonic pasteurellosis. Aerosolization or subcutaneous vaccination with live *P. haemolytica* or *P. multocida* produced decreased severity of lung lesions induced by transthoracic challenge (Corstvet et al., 1978, Amer. Assoc. Vet. Lab. Diag., 21:67–90; Newman et al., 1982, Am. J. Vet. Res., 43:417–422), as compared to unvaccinated controls. One of the most interesting points about one of those studies (Newman et al.) was that resistance (probably mediated by more efficient phagocytosis by pulmonary macrophages) was greater in aerosol vaccinated than in subcutaneously vaccinated calves. Subsequent studies with goats inoculated in the lung with live *P. haemolytica* embedded in agar beads yielded a high degree of immunity (Purdy et al., 1990, Am. J. Vet. Res., 51:1629–1634). The vaccinated animals were better protected than controls against a transthoracic challenge of *P. haemolytica* ($1\times10^7$ CFU) injected into the lung of each.

Confer et al. disclosed that vaccination with live *P. haemolytica* produced an increase in antibody titer to somatic antigens (LPS), leukotoxin (LKT) and a capsular-carbohydrate antigen (CPS) (Lessley, et al., 1985, Vet. Immunol. Immunopathol., 10:279–296). Subsequent reports have shown that elevated serum antibody titers to the *P. haemolytica* LKT or the CPS correlate well with enhanced resistance to experimental *P. haemolytica* challenge (Confer et al., 1984, Am. J. Vet. Res., 46:2543–2545, Confer et al., 1985, Am. J. Vet. Res., 46:342–347, Pancier et al., 1984, Am. J. Vet. Res., 45:2538–2542, Gentry et al., 1985, Vet. Immunol. Immunopath., 9:239–250). Confer et al. (1985, Vet. Immunol. Immunopath. 10:265–278) examined serum antibodies to antigens derived from a saline extract of Ph 1 and demonstrated a positive correlation with resistance to experimental bovine pneumonic pasteurellosis to several of the antigens. Their data suggested that antibody to polysaccharide antigens may be important to resistance. This led to the incorporation of several of these antigens, LPS, CPS, and LKT, in a subunit agar-bead vaccine (Purdy et al., 1993, Amer. J. Vet. Res., 54:1637–1647). LKT, a heat-labile protein toxin produced by *P. haemolytica,* has been considered a virulence factor for the organism because of its ability to exert a negative effect on bovine alveolar macrophages and neutrophils (Wilkie, 1982, J. Am. Vet. Med. Assoc., 181:1074–1079). LPS produced by *P. haemolytica* may be important in bovine pulmonary pasteurellosis. Confer and Simon, (1986, Am. J. Vet. Res., 47:154–157), recently demonstrated biological activity of *P. haemolytica* LPS for bovine leukocytes in vitro but declared that further studies are required to decide whether it plays a role in the production of the lung lesions seen in pneumonic pasteurellosis. Slocombe et al. (1990, Am. J. Vet. Res., 51:433–438) demonstrated that Ph 1 endotoxin is pathogenic when delivered intravenously (IV) and by airway routes. They showed that intratracheal inoculation of Ph 1 LPS caused hypoxemia and increased the alveolar-arterial oxygen differences. By contrast, IV inoculation of Ph 1 and LPS caused systemic hypotension, leukopenia, and gas exchange impairment. Both routes of inoculation were associated with areas of pulmonary hemorrhage, edema and acute inflammation. In addition, Breider et al. (1990, Infect. Immun., 58:1671–1677) showed that *P. haemolytica* produces a soluble factor that appears to be LPS and is directly toxic to bovine pulmonary endothelial cells. However, Confer et al. (1986, Amer. J. Vet. Res., 47:1134–1138) examined serum antibodies to *P. haemolytica* LPS and their relationship to experimental bovine pneumonic pasteurellosis, and they concluded that serum antibody responses to Ph 1 LPS did not seem important for resistance to challenge. They showed no significant correlation between the lung lesion score and antibody response to Ph 1 LPS. This is essentially the same conclusion that was reached by Purdy et al. (1993, ibid), regarding the protective effect of antibodies directed against Ph A1 LPS.

The importance of the CPS in infections caused by *P. haemolytica* has been known for a long time. The presence of soluble capsular material on *P. haemolytica* was first demonstrated in 1956 (Carter, 1956, Can. J. Microbiol., 2:485–488) and it was shown to be carbohydrate. Later, capsular material was extracted from *P. haemolytica* by a variety of different techniques (Evans and Wells, 1979, Res. Vet. Sci., 27:213–217; Gentry et al., 1982, Am. J. Vet. Res., 43:2070–2073; Tadayan and Lauerman, 1981, Vet. Microbiol., 6:85–93) and vaccination of mice, hamsters, and sheep (Wells et al., 1979, Res. Vet. Sci., 27:248–250, Gilmore et al., 1979, Vet. Rec., 104:15) with these extracts protected against experimental challenge with this organism. However, subsequent studies (Purdy et al., 1993, ibid; Purdy et al., 1991, Abstracts, Conference of Research Workers in Animal Disease, #113, p. 20; Conlon et al., 1991, Infect. Immun., 59:587–591; Conlon and Shewen, 1991, Abstracts, Conference of Research Workers in Animal Disease, #277, p. 49) have indicated that a subunit vaccine would not provide adequate protection against a substantial Ph 1 challenge. Transthoracic immunization with Ph 1 LPS and recombinant cytotoxin offered no protection against a subsequent transthoracic challenge. Initial experiments with Ph 1 CPS demonstrated some protection against a subsequent Ph 1 challenge but it was not significant. When these studies were repeated (Purdy et al., 1993, ibid; Purdy et al. 1991, ibid) no protective effect was exhibited. Others have had a similar lack of success with subunit vaccines. Conlon et al. (ibid) decided in their study with recombinant leukotoxin from Ph 1 and cattle that, "although LKT is an important virulence factor for the organisms, an immune response to LKT alone does not protect animals against disease". These same workers (Conlon and Shewen, ibid) also showed that a purified Ph 1-CPS vaccine offered no protection against a subsequent Ph 1 challenge in cattle.

Lo and MacDonald (1991, Mutation Res., 263:159–163) demonstrated that *P. haemolytica* is highly sensitive to ultraviolet radiation, and suggested that the bacterium lacks some of the important mechanisms to repair UV-induced damage. Whitely et al. (1991, Vet. Pathol., 28:275–285) examined alterations in pulmonary morphology and peripheral coagulation profiles caused by intratracheal inoculation of live and ultraviolet light-killed Ph 1 in cattle. These authors showed that UV-killed bacteria were capable of causing fibrin exudation, platelet aggregation, and alveolar epithelial damage similar to live bacteria, but the degenerative changes in neutrophils, endothelial cells and intravascular fibrin formation that were observed with the live Ph 1, were not seen.

SUMMARY OF THE INVENTION

We have now discovered a novel vaccine for immunizing animals against *Pasteurella haemolytica* infection. The vaccine is composed of whole killed cells of *P. haemolytica* in a dosage effective to immunize an animal against the organism, in combination with a pharmaceutically acceptable carrier. The killed cells of *P. haemolytica* are produced by irradiating viable cells with ultraviolet light for a sufficient period of time to kill the cells.

In accordance with this discovery, it is an object of this invention to provide a novel vaccine protective against Pasteurella infection in animals.

It is also an object to provide an improved vaccine against *P. haemolytica* which offers both superior protection and safety over existing vaccines.

Another object of the invention is to provide a vaccine against *P. haemolytica* which exhibits sustained exposure to the antigens over an extended period of time, extending the duration of the protective immune response.

Other objects and advantages of the invention will become readily apparent from the ensuing description.

DETAILED DESCRIPTION OF THE INVENTION

Figure 1:
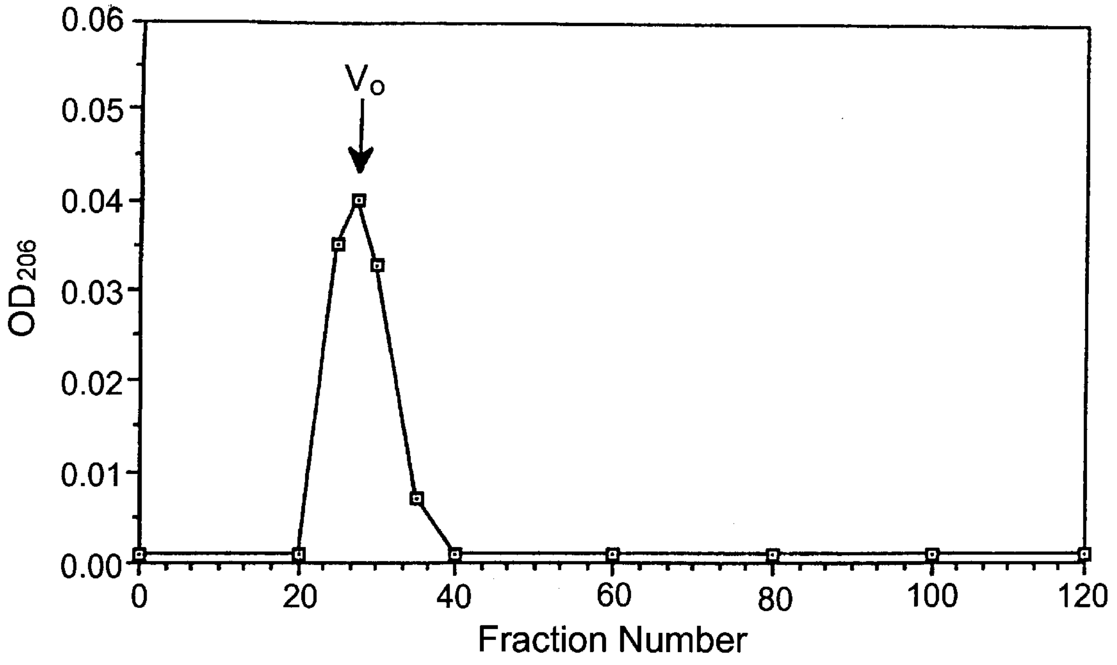
FIG. 1. Elution profile from Example 1 of the purified capsule carbohydrate of *P. haemolytica* A1 on Sepharose 2B employing 0.01 mM Tris-HCl buffer, pH 8.0. These eluate was monitored continuously for capsule carbohydrate by absorbance (OD) at 206 nm. $V_0$=void volume of the column.

The vaccine of this invention is effective for controlling *Pasteurella haemolytica* infections in a variety of animals when administered thereto. Without being limited thereto, the vaccine is especially beneficial for the treatment of ruminants, both domestic and exotic, and particularly bovine, sheep and goats.

The inventive vaccine is a killed cell preparation or bacterin. To produce the vaccine, viable cells of *P. haemolytica* are exposed to ultraviolet light for a sufficient period of time to kill 100% of the cells. We have unexpectedly found that cells of *P. haemolytica* may be killed by exposure to ultraviolet light while still retaining their antigenicity, that is, their ability to elicit a protective immune response. Although the radiation severely damages the cell's DNA, cellular proteins and carbohydrates are not affected. Effective ultraviolet wavelengths and exposure periods are defined herein as those which kill 100% of the *P. haemolytica* cells treated, while retaining the ability of the treated cells to elicit a protective immune response. The wavelength and exposure time are not critical, and may be readily determined by the practitioner skilled in the art. Preferred wavelengths of the radiation include, but are not limited to, between about 185 to 360 nm and particularly between about 190 to 320 nm. The exposure period for a given treatment may vary with the particular wavelength chosen, the path length of the medium containing the cells (i.e., the depth through which the light must pass) and the presence of contaminants or other UV absorbing components in the medium. Suitable exposure times for a particular wavelength to achieve 100% killing may be readily determined from lethal killing curves of % killed vs. time of treatment. We have discovered that irradiation for periods beyond those required for 100% killing is not harmful and does not negatively impact immunogenicity. The temperature of the treatment also is not critical, although very high temperatures inducing protein denaturization should be obviously avoided. Temperatures between about 4 to 11° C. are preferred.

Propogation of *P. haemolytica* in preparation for irradiation may be accomplished using conventional techniques and culture media known in the art. A variety of both solid and liquid culture media may be suitable for use herein, and include but are not limited to chocolate agar, MacConkey agar and preferably blood agar and brain-heart infusion broth (BHI). Culture on solid blood agar medium is particularly preferred, allowing for the preparation of highly concentrated suspensions. Following culture on solid media, the cells may be harvested by suspension in a small amount of a suitable carrier, such as PBS. When using liquid culture media, the cells may be optionally concentrated, for example, by filtration or centrifugation, to obtain a high density suspension of cells.

The irradiation process of this invention may be used to prepare vaccines to any serotype of either the A or T biotype of *P. haemolytica.* However, the invention is particularly valuable for the preparation of vaccines to the A biotype, and especially the A1 serotype, which is most frequently implicated as the causative agent of pneumonic pasteurellosis in the bovine species.

Following irradiation, the killed *P. haemolytica* cells are prepared for administration by formulation in an effective immunization dosage with a pharmaceutically acceptable carrier. An effective immunization dosage is defined herein as being that amount which will induce complete or partial immunity (elicit a protective immune response) in a treated animal against subsequent challenge with virulent *P. haemolytica.* Immunity is considered as having been induced in a population of treated animals when the level of protection for the population is significantly higher than that of an unvaccinated control group. The appropriate effective dosage can be readily determined by the practitioner skilled in the art. Typically, the vaccine will contain at least about $10^6$ cells of *P. haemolytica,* preferably between about $10^8$ to $10^{12}$ cells, and most preferably between about $10^{10}$ to $10^{12}$ cells. Although greater amounts of cells may be administered, production of the necessary highly concentrated formulations is generally impractical.

The killed cells are prepared for administration by formulation in a pharmaceutically acceptable carrier such as physiological saline, mineral oil, vegetable oils, aqueous sodium carboxymethyl cellulose, or aqueous polyvinylpyrrolidone. The vaccine formulations may also contain optional adjuvants, antibacterial agents or other pharmaceutically active agents as are conventional in the art. Without being limited thereto, suitable adjuvants include but are not limited to mineral oil, vegetable oils, alum, Freund's incomplete adjuvant, or Freund's incomplete adjuvant, with oils and Freund's incomplete adjuvant being particularly preferred. Still other preferred adjuvants include microparticles or beads of biocompatible matrix materials. We have unexpectedly discovered that such microparticles function as immunopotentiators when admixed with the killed cell formulations prior to administration. The microparticles may be composed of any biocompatible matrix materials as are conventional in the art, including but not limited to, agar and polyarylate. The practitioner skilled in the art will recognize that other carriers or adjuvants may be used as well. For example, other adjuvants which may be used are described by Webb and Winkelstein [in Basic & Clinical Immunology, Stites et al. (ed.), fifth edition, Lange Medical Publications, Los Altos, Calif., 1984, pages 282–285], the contents of which are incorporated by reference herein.

In accordance with a preferred embodiment, the killed cells may be incorporated into microparticles or microcapsules to prolong the exposure of the antigenic material to the subject animal and hence protect the animal against infection for long periods of time. The microparticles and capsules may be formed from a variety of well-known inert, biocompatible matrix materials using techniques conventional in the art. Without being limited thereto, suitable matrix materials include natural or synthetic polymers such as alginates, poly(lactic acid), poly(lactic/glycolic acid), poly(caprolactone), polycarbonates, polyamides, polyanhydrides, polyortho esters, polyacetals, polycyanoacrylates, polyurethanes, ethytlene-vinyl acetate copolymers, polystyrenes, polyvinyl chloride, polyvinyl fluoride, poly(vinyl imidazole), chlorosulphonated polyolefins, polyethylene oxide, and particularly agar and polyacrylates. Examples of techniques for incorporation of materials into microparticles or encapsulation which may be used herein are described by Sparks [Microencapsulation, In: Kirk-Othmer Encyclopedia of Chemical Technology, third edition, John Wiley & Sons, New York, (1981) volume 15, pages 470–493], Kydonius [Controlled Release Technologies: Methods, Theories, and Applications, CRC Press, Cleveland, Ohio, 1980], and El-Nokaly et al, (ed.) [Polymeric Delivery Systems, Properties and Applications, ACS Sumposium Series 520, American Chemical Society, Washington, D.C., 1993], the contents of each of which are incorporated by reference herein.

The vaccines of the invention may be administered to the subject animal by any convenient route which enables the cells to elicit an immune response, such as by subcutaneous, intramuscular or transthoracic injection, or by aerosol. However, subcutaneous injection is preferred for practical considerations. The vaccine may be administered in a single dose or in a plurality of doses. In accordance with a preferred embodiment, the vaccine may be administered in two doses about 2 to 6 weeks apart, most preferably about 2–3 weeks apart. The subject animals may be vaccinated at any time, although it is preferred to administer the vaccine shortly (optimally about 10 days to two weeks) before periods of anticipated stress, such as during shipping or other handling. It is also envisioned that the vaccine may be administered to pregnant animals prior to birth to increase production of hyperimmune colostrum.

The following examples are intended only to further illustrate the invention and are not intended to limit the scope of the invention which is defined by the claims.

Example 1

Fifty weanling male Spanish goats were purchased from one herd located near Brady, Tex. These weanling goats had no history of respiratory disease or of being vaccinated with Pasteurella products. They were transported 644 km by truck to the United States Department of Agriculture, Agriculture Research Service, Research Laboratory located in Bushland, Tex. The goats were treated for internal parasites (Ivomec-MSD AGVET, Merck & Co. Inc., Rahway, N.J.) and coccidia (Amprolium, MSD AGVET, Merck & Co. Inc., Rahway, N.J.) and conditioned for three weeks to their new environment. They were housed in a covered three sided barn and were maintained on a pelleted sheep/goat ration (0.45 kg/goat/day), alfalfa hay and fresh water. Goat body weights were recorded on days −21, 0, 7, 21, and 34.

Preparation of Ph 1 Subunit Capsule Antigens

The Ph 1 capsule (CPS) was purified as previously described (Purdy et al. 1993, ibid). Protein contamination of the capsule material was quantified by the method of Lowry (1951, J. Biol. Chem., 193:265–270) using bovine serum albumin as the standard. Nucleic acid content was measured by the procedure described by Kabat and Mayer (1961, Experimental Immunochemistry, 2nd ed., Charles C. Thomas, Springfield, Ill.) using yeast RNA as a standard. Two-keto-3-deoxyoctonate was quantified by the thiobarbituric acid assay of Osborn (1963, Proc. Natl. Acad. Sci., 50:499–506. The purified product was freeze-dried and stored in an air tight vial in the refrigerator.

Agar Bead Preparation

Agar beads were impregnated with Ph 1 capsule antigen, ultraviolet killed Ph 1 bacterin or live Ph 1 vaccine, using a method previously described (Cash et al., 1983, Can. J. Microbiol., 29:448–456). Briefly, 1 part of the antigen is mixed with 9 parts of molten agar (46° C.). This mixture is poured into warmed (46° C.) heavy mineral oil, immediately placed on ice, and vigorously stirred with a magnetic stir bar until the beads are formed, then the beads are separated from the oil. In one bacterin group (Ph 1-0), the ultraviolet killed Ph 1 was only mixed with the agar beads and not impregnated inside them. This was done to determine if similar results would be obtained without placing the bacteria inside the beads as others have reported (Nacucchio et al., 1984, Pediatr. Res., 18:295–296).

Bacterium

*Pasteurella haemolytica* A1 was isolated from a pneumonic calf and it was identified by colony morphology, Gram's staining, biochemical test, and by using a specific serotyping antiserum (Frank and Wessman, 1978, J. Clin. Microbiol., 7:142–145).

Live Vaccine, Challenge Inoculation and Bacterin Preparations

Live Ph 1 vaccine and challenge-inoculum cultures (Purdy et al., 1990, Am. J. Vet. Res., 51:1629–1634) were routinely grown on nutrient agar plus 5% bovine (citrate blood for 16 hours at 37° C. in a 5% $CO_2$ environment in a water jacketed incubator. Cultures were harvested in phosphate-buffered saline solution (0.10 M, pH 7.2) and the bacterial concentration was determined by culturing on nutrient agar plus 5% bovine (citrate) blood for 16 hours at 37° C. to determine the colony-forming units (CPU)/ml by surface colony counts.

The bacterin cultures were grown on nutrient agar plus 5% goat blood at 37° C. in a 5% $CO_2$ atmosphere for 10 hours. Cultures were harvested in physiologic saline solution (0.15 M, pH 6.6) and the CFU/ml were counted as previously described. The bacterial suspension (for ultraviolet irradiation) was dispensed into sterile petri plates to a depth of 5 mm and irradiated (Spectroline model TR-312 A Ultraviolet transilluminator, Spectronics Corp., Westburry, N.Y.) at 315 nm for 60 minutes inside a vertical laminar flow biological hood, with the petri plate lids removed. After irradiation, fluid lost due to evaporation was replaced with sterile water by washing out the petri plates containing the bacterial suspension. The irradiated bacterial suspension was repeatedly cultured to insure that no Ph 1 survived the treatment.

Experimental Design

Thirty-eight of the goats were randomly allotted to 6 treatment groups: 1) positive control (PC, n=8), live Ph 1 impregnated inside agar beads; 2) negative controls (NC, n=6), agar beads only; 3) capsule (CPS, n=6), antigen impregnated inside agar beads; 4) ultraviolet killed bacterin (Ph 1-0, n=6), whole cells mixed with agar beads; 5) ultraviolet killed bacterin (Ph 1-I, n=6), whole cells impregnated inside agar beads; and 6) ultraviolet killed bacterin (Ph 1-I-SC, n=6), whole cells impregnated into agar beads and injected subcutaneously into the left thigh. The goats of the first 5 groups were each injected transthoracicly into the left posterior lung lobe with the appropriate antigen, bacterin or live vaccine-agar bead preparation. All goats were treated twice, 21 days apart.

Prior to live Ph 1 injections, the PC goats were moved and held in a separate barn. This was done to prevent any possible Ph 1 cross contamination to other goat groups. Goats in groups 1 through 5 were tranquilized (100 mg thylisobutrazine HCL, IV., Diquel, Jensen Salsbery Laboratories, Division of Burroughs Wellcome Co., Kansas City, Mo.) 15 minutes before the injection into the lung (Purdy et al., 1990, ibid).

The concentrations and doses of the antigen, bacterins, or live Ph 1 vaccine given on day 0 were: $2.28 \times 10^6$ Ph 1 CFU/ml/goat (PC); agar beads only suspended in physiologic saline solution 1 ml/goat (NC); 54 mg capsule antigen impregnated inside agar beads 1 ml/goat (CPS); $1.4 \times 10^9$ ultraviolet killed Ph 1 CFU/ml/goat (Ph 1-0); $8 \times 10^9$ ultraviolet killed Ph 1 CFU/ml/goat (Ph 1-I) and Ph 1-I-SC). The CPS concentration and ultraviolet killed Ph 1 bacterin dose, on day 21 was the same. The positive control goats on day 21 were each given $1.25 \times 10^6$ Ph 1 CFU/ml/goat.

All goats were challenge exposed on day 34 by transthoracic injection of live Ph 1 (1 ml dose, $1.93 \times 10^8$ CFU) into the right posterior lung lobe. On day 38 they were euthanatized with an overdose of barbiturate anesthetic and immediately exsanguinated (Purdy et al, 1990, ibid). Necropsies were performed, and lungs were examined for Ph 1-induced lesions. Consolidated lesions were measured (length×width×thickness) with calipers. Immune protection was determined on the basis of the volume of consolidated lung tissue four days after transthoracic challenge. Smaller lung lesions were expected in goats that had protective immunity at the time of transthoracic challenge.

Specimen Collection

Blood samples were collected via jugular venipuncture on day 0, then every week. A heparinized anticoagulated blood sample (3 ml) was used for total white blood cell (WBC) counts, packed cell volume (PCV), and WBC differential counts. Sera were collected from clotted blood samples (25 ml). The blood was allowed to clot at ambient temperature for approximately 20 minutes, placed on ice for 1 hour, and centrifuged at 4° C. The serum from each goat was decanted into three cold glass vials which were immediately frozen at −80° C. These serum samples were used to determine complement activity Ph 1 IHA antibody and anticytotoxin neutralization titers.

Cotton swabs were used to collect nasal turbinate mucus specimens on days 0–3, 6, 7, 10, 14, 21, 34–38. The specimens were frozen and stored at −85° C. After thawing, they were subject to bacteriologic culture on 5% bovine blood agar and incubated at 37° C. in a 5% $CO_2$ atmosphere. *Pasteurella haemolytica* isolates were identified by appearance of colony morphology, hemolysis, Gram's staining, and specific serotyping.

At necropsy, bacterial specimens were obtained for culture by aseptically inserting a sterile cotton swab through an incision at the challenge injection site. Specimens were similarly taken from the right lung, and trachea after it was severed from the larynx. After the swab had absorbed tissue fluid (approximately 0.1 ml) from the lung, it was removed and expressed into a tube. Serial 10-fold dilutions were created. A 0.1 ml sample of each dilution was spread onto a blood agar plate, incubated at 37° C. for 16 hours in a 5% $CO_2$ atmosphere, and colonies of Ph 1 were counted. Before a swab was inserted into the left lung tissue for isolation purposes, the right tracheal branch of the lung was clamped off with a hemostat and 2000 ml of sterile physiologic saline solution was infused into the left lung. This lung was massaged, inverted and approximately 50 to 100 ml of liquid was recovered for potential surface antibody.

Clinical Observations

Physical examinations were performed and rectal temperatures were recorded for all goats on days 0–3, 6–10, 14, 20–23, and 34–38. In addition the goats were observed twice a day for adverse clinical signs throughout the experiment. The goats were always treated humanely and in accordance with the Consortium Guide (1988).

Serum Assays

An anticytotoxin bioassay (CT neutralization) (Chang et al., 1987, Infect. and Immun., 55:2348–2354) was used with modification and is briefly described. The assay used bovine lymphoma cells (BL3) as target cells and was performed in 96 well micro-titer plates. Stock cytotoxin was titered prior to each use. One unit of toxin was defined as that quantity which causes complete lysis of $1\times10^6$ BL3 cells. Sera were diluted in L15 media by doubling dilutions, then toxin was added 1:1. Antisera (100 microliters)-toxin (100 microliter) mixtures were incubated at room temperature for 10 minutes. Approximately 15,000 BL3 cells (100 microliters) suspended in L15 media were then added to each well. Plates were incubated for 1 hour at 37° C. in a 5% $CO_2$ atmosphere and examined by microscopy for lysis of BL3 cells. The titer end-point of the antisera was determined as the last dilution which gave >90% protection. Two control sera were used in each microliter plate (positive control—1:2048 anticytotoxin titer and negative control fetal calf serum—no anticytotoxin activity). All serum samples from each animal were tested on the same day.

A standard serum classical hemolytic complement assay (Renshaw et al., 1980, Classical and Alternate Complement Pathway Activities in Sera from Colostrum-fed Calves During the Initial Three Days After Birth, In:Proc. 3rd Int. Symp. Neonatal Diarrhea, 3:161–171) was conducted and reported in mean CH50 units/ml of serum. All samples collected on the evaluation days from each goat were assayed on the same day. A laboratory bovine serum control (stored at −85° C.) was included with each assay to determine daily test variation.

Statistical Analysis

Data were analyzed by analysis of variance using the general linear models procedure of the statistical analysis system (SAS), (SAS User's Guide, 1988), Differences among treatments and sampling days were compared by Duncan's multiple-range test if a significant F-test was obtained. Differences were considered statistically significant at P<0.05. Anticytotoxin antibody titers and IHA antibody titers are reported as geometric means.

Antigen Characterization

There was no detectable protein or nucleic acid in the CPS preparation. There was also no detectable 2-keto-3-deoxyoctonate indicating no contaminating LPS. Three mg of Ph 1 CPS gave only one homogenous peak which eluted from the Sepharose 2B column in the void volume, indicating a very high molecular weight (FIG. 1). Silver stained gels of the purified CPS indicated material with a very high molecular weight which did not contain any LPS (Purdy et al., 1993, ibid).

Rectal Temperature Recordings

Figure 2:
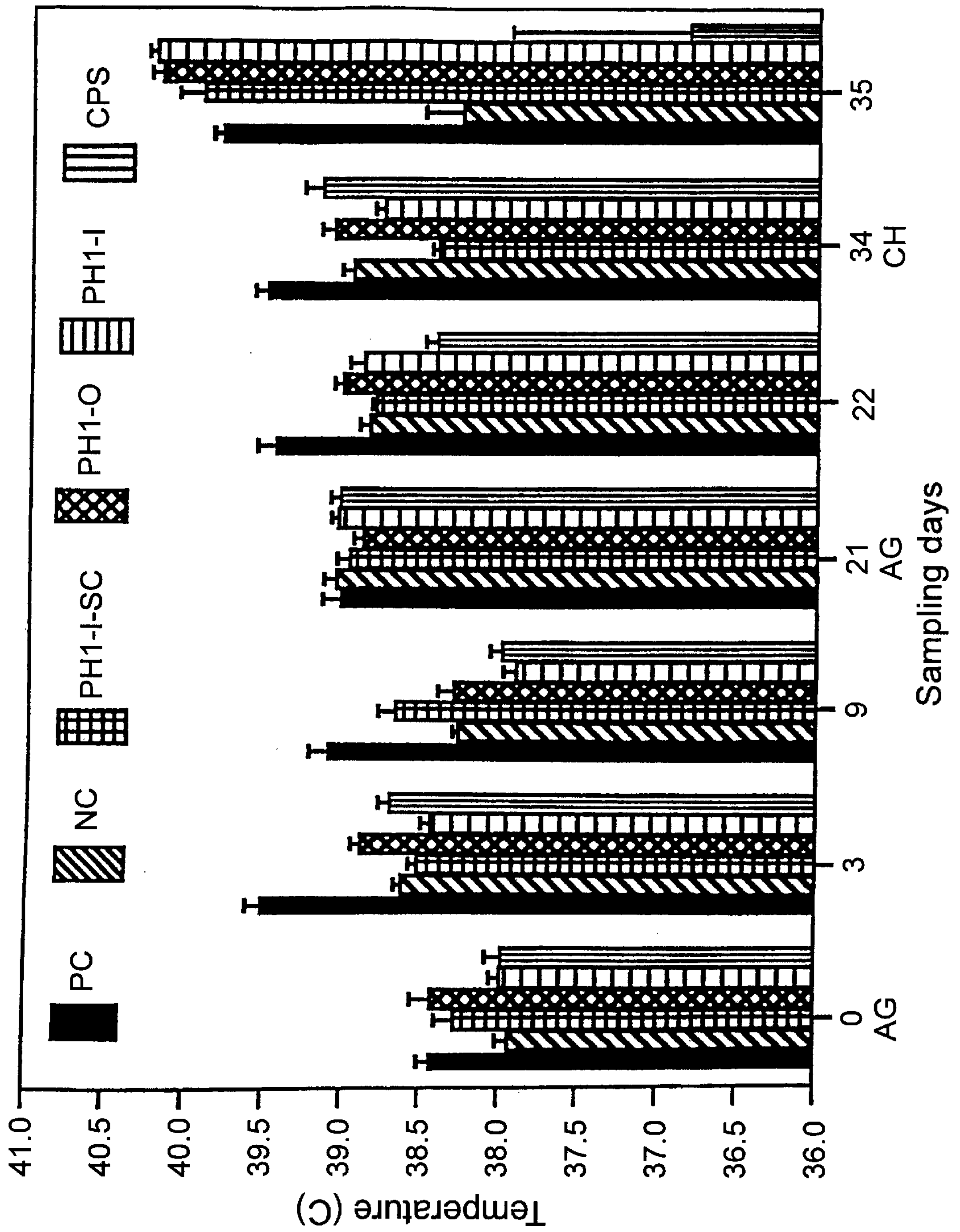
FIG. 2. Mean rectal temperature of goats treated with *P. haemolytica* A1 (Ph 1) vaccines in Example 1.

There were significant differences in rectal temperature among treatment groups on days 3 (P=0.0001), 7 (P=0.001), 8 (P=0.0002), 9 (P=0.0007), 24 (P=0.006), and 34 (P=0.003) (FIG. 2). Body temperature increased within 24 hours after the first live Ph 1 injection of the lungs (PC group) and in some cases, it lasted for a few days. Three goats in the PC group died two days after the first injection form an induced Ph 1 pneumonia which overwhelmed them. After challenge exposure, the greatest increase in body temperature occurred in the Ph 1-0, Ph 1-I, Ph 1-I-SC groups and a subnormal temperature was noted in the negative control and CPS groups. The latter two groups had goats dying from the challenge exposure.

Weight Data

The mean body weight of the goats on day −21 was 10.43 kg (range 9.8 to 11.3 kg). There was no significant differences in weight gain among treatment groups. The mean body weight of the goats on the challenge exposure day 34 was 16.2 kg.

Total White Blood Cell Counts

Figures 3A, 3B:
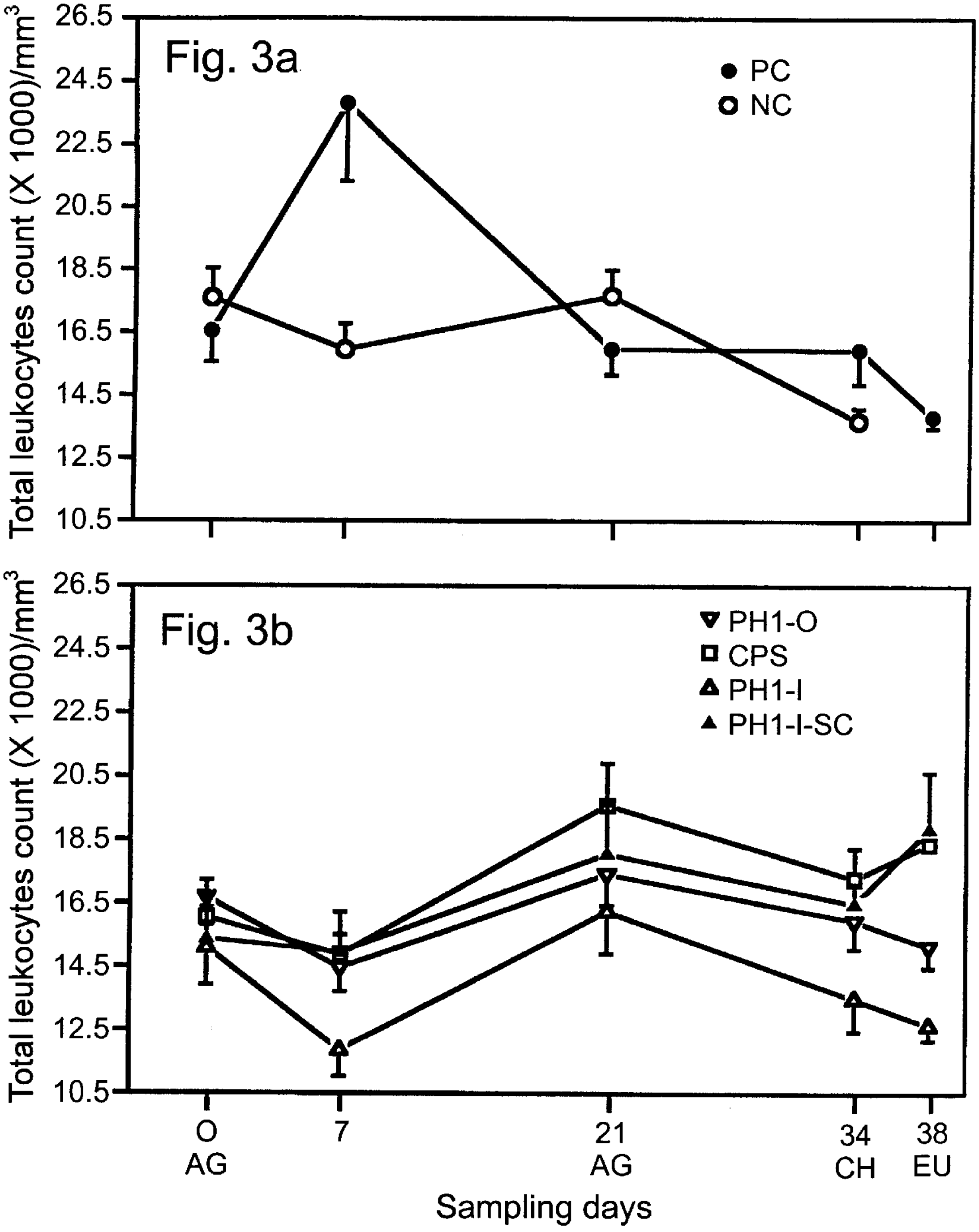
FIGS. 3(*a*) and (*b*). Mean WBC count/mm$^3$ of goats treated in Example 1.

There were significant differences in total WBC counts among treatment groups (FIG. 3) on day 7 (P=0.045) due to an increase of 7,242 cells (23,780) in the PC group. The range of WBC counts on day 7 in all groups except the PC group was 11,858 to 15,933. No significant differences in total WBC counts occurred among days in any treatment group.

Serum Anticytotoxin Antibodies

Figures 4A, 4B:
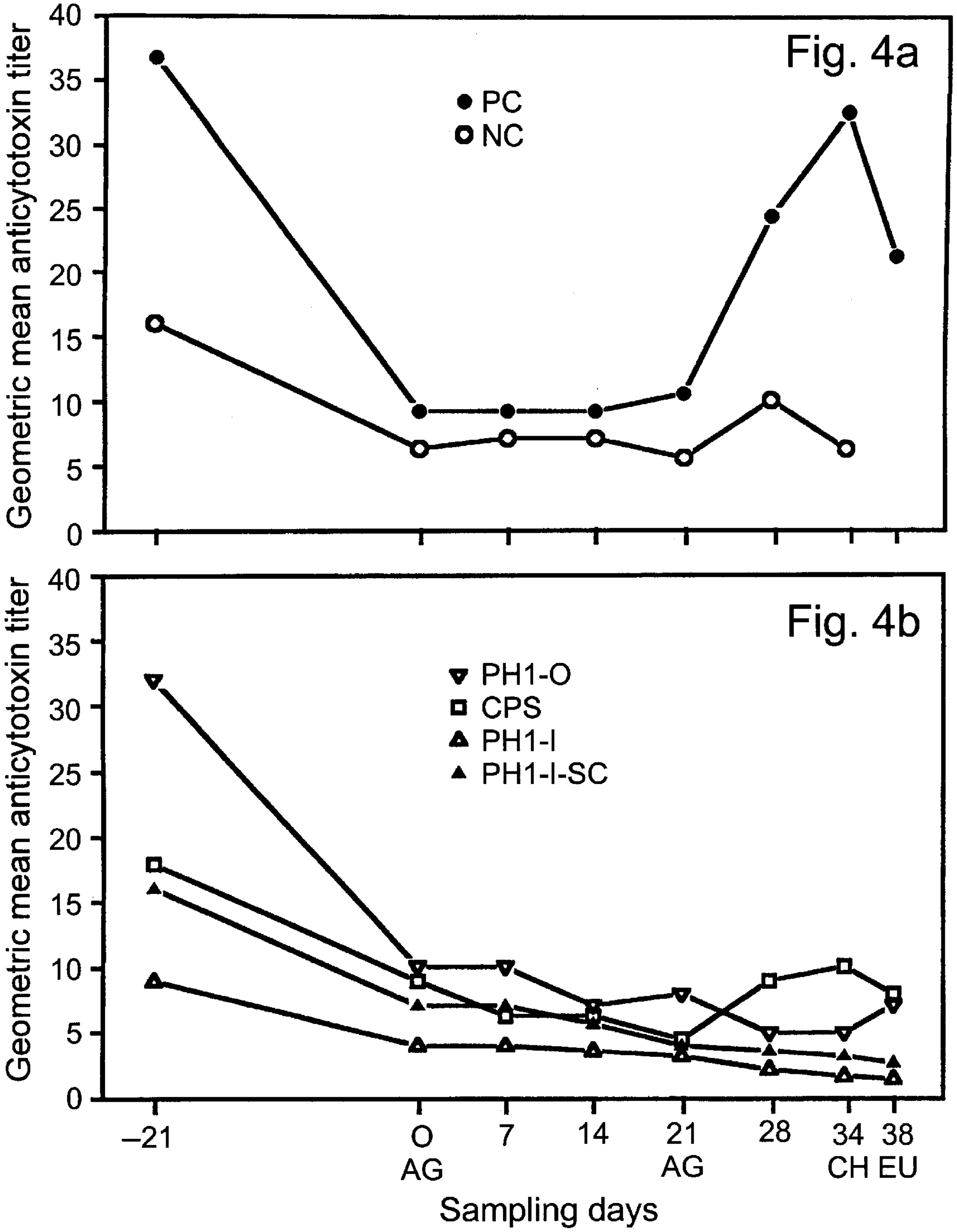
FIGS. 4(*a*) and (*b*). Anticytotoxin antibody titer (geometric mean) of goats treated in Example 1.

Passive antibody decreased from day −21 to day 0 in all groups (FIG. 4). The only group to have an increase in active anticytotoxin antibody after two vaccinations was the PC group which received live Ph 1. The PC mean group titer was maximum on day 34, 13 days after the second vaccination.

Serum Hemolytic Complement Activity

Figures 5A, 5B:
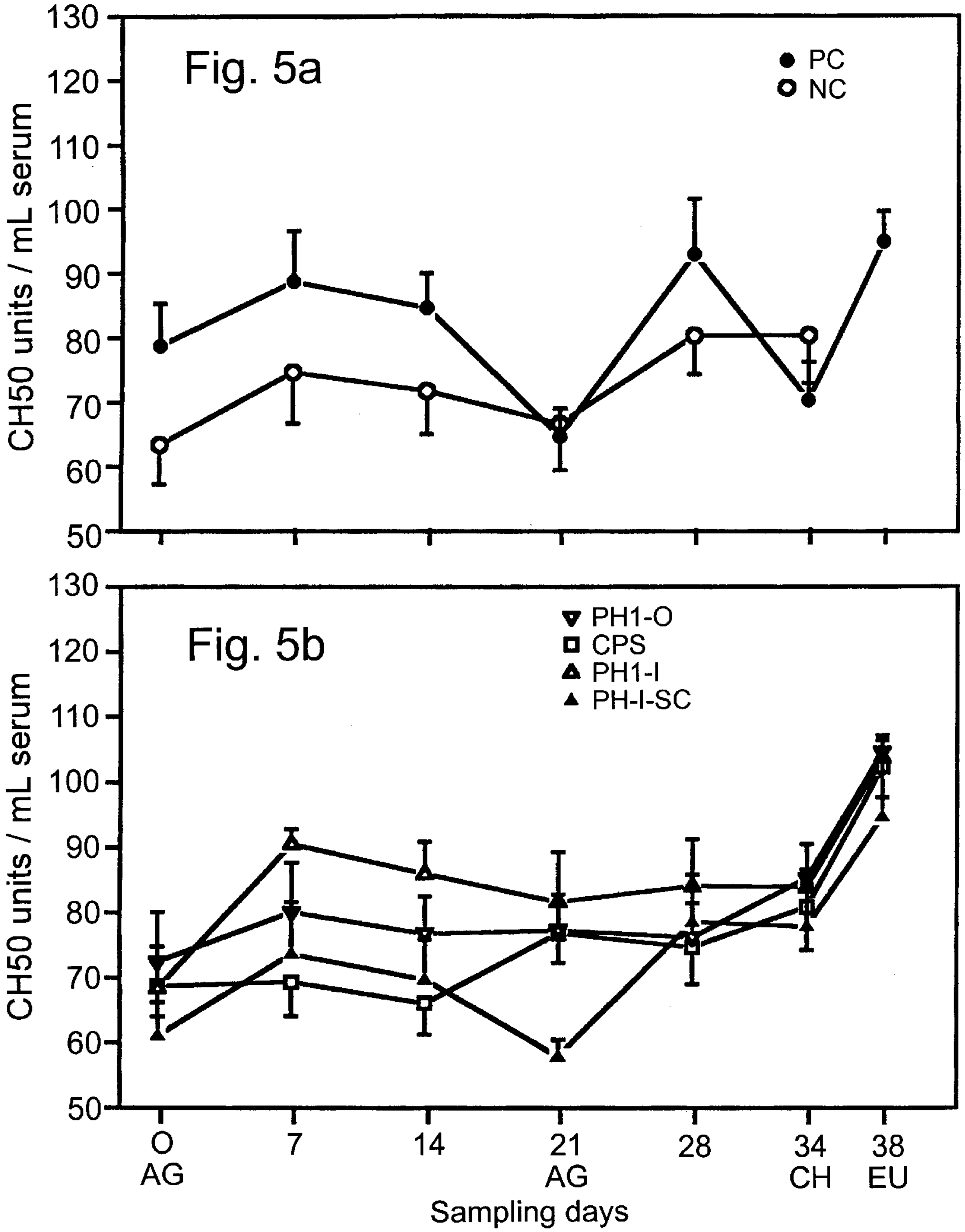
FIGS. 5(*a*) and (*b*). Mean serum complement activity ($CH_{50}$ units/ml) of goats treated in Example 1.

There were significant differences in mean complement activity among treatment groups (FIG. 5) on day 21 (P=0.049). Significant differences in complement activity occurred among days in all groups except the NC group. The average CH50 units/ml of serum for all treatment groups over all sampling days was 78 with a range of 72 to 85. There was a trend for the complement activity to increase in all surviving groups after the challenge exposure, and it was significant in 3 of the 5 groups.

Serum Ph 1 IHA Antibodies

Figures 6A, 6B:
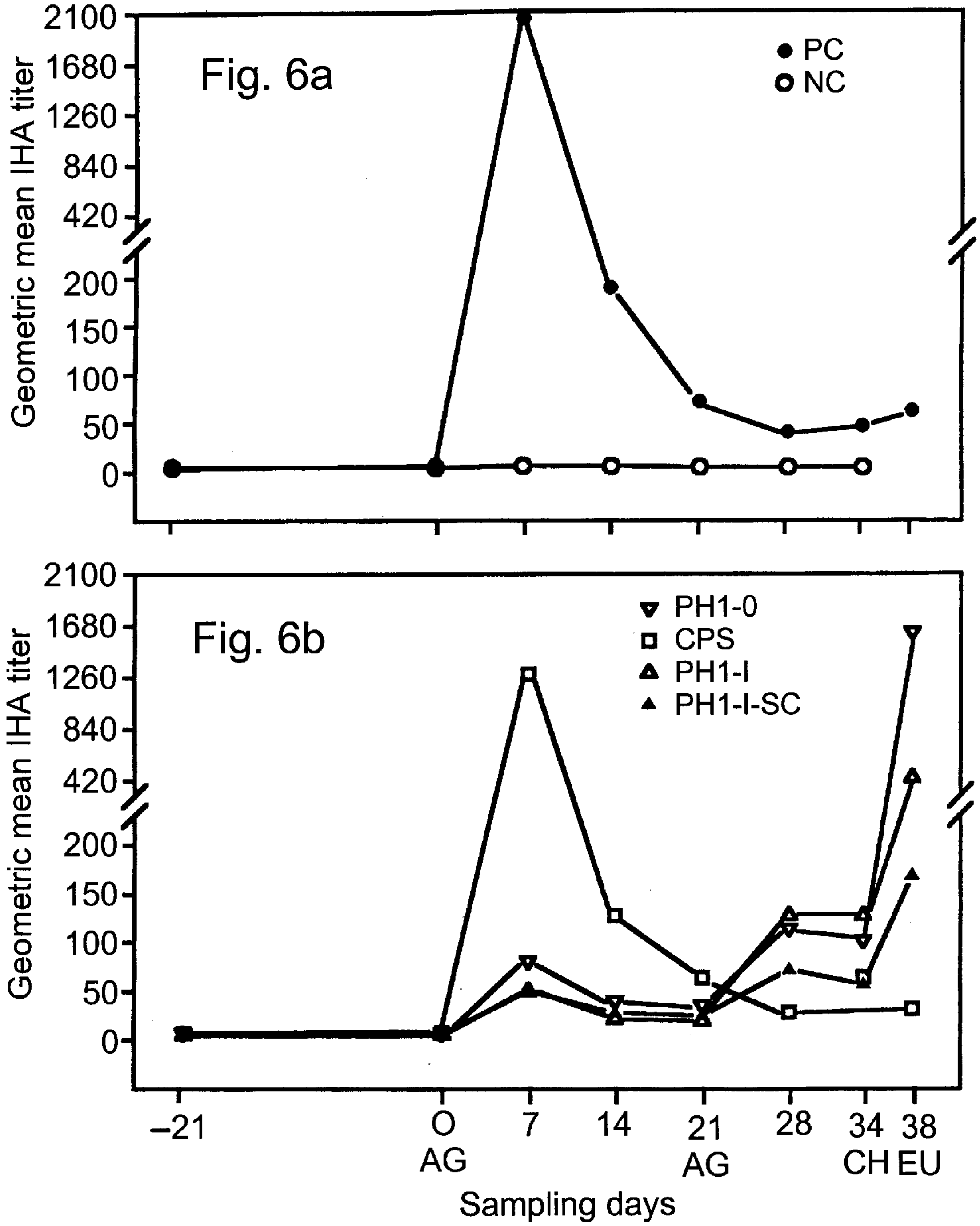
FIGS. 6(*a*) and (*b*). Indirect hemagglutination antibody titer (geometric mean) of goats treated in Example 1.

The geometric mean Ph 1 IHA antibody titer of all groups was low (<1:9) on day −21 and <1:2 for all six treatment groups on day 0 (FIG. 6). Seven days after the first antigen injection a primary antibody response was seen in all groups. It was maximal in the PC (1:2048) and the CPS (1:1290) groups. A five-fold IHA antibody titer increase was seen in the Ph 1-I group after the second antigen injection. The antibody titers of two groups (PC and CPS) were suppressed after the second antigen injection and after the challenge exposure. During the same time period Ph 1-I and Ph 1-I-SC group mean antibody titers rose slowly. The Ph 1-O group had over a ten-fold mean antibody increase after challenge exposure. The Ph 1 IHA antibody titer of the NC group remained low (<1:8) on all sampling days.

Pasteurella Isolation

Excluding the PC group, no Ph 1 isolates (out of 240 attempts) were recovered from the nasal turbinates of the treatment groups prior to the second antigen injection. Two Ph 2 isolates were recovered from one NC goat on days 7 and 10, and 3 Ph 2 isolates were recovered from one PC goat on days 2,6, and 10. There were 8 Ph 1 isolates recovered from three PC goats on days 6, 7, 10, 14, and 21. Also, Ph 1 isolates were recovered from the turbinates of 2 of 3 PC goats which died of Ph 1 induced pneumonia 2 days after inoculation of their lungs with live Ph 1. After the second antigen inoculation and prior to challenge exposure 2 Ph 1 isolates were recovered from one NC goat on day 24 and one PC goat on day 23; one *Pasteurella multocida* isolate (out of 108 attempts) was recovered from one Ph 1-I-SC goat on day 24.

After challenge exposure, one Ph 1 isolate (out of 20 attempts) was recovered from the nasal turbinates of 2 PC goats on days 35 and 37. Eight Ph 1 isolates (out of 24 attempts) were recovered from the nasal turbinates of 3 Ph 1-O goats. Ten Ph 1 isolates (out of 20 attempts) were recovered from 4 of 5 goats in the Ph 1-I group. Ten Ph 1 isolates were recovered (out of 22 attempts) from 5 of 6 goats in the Ph 1-I-SC group. Five Ph 1 isolates (out of 6 attempts) were recovered from 6 goats in the NC group. Four Ph 1 isolates (out of 11 attempts) were recovered from 6 goats in the CPS group.

*Pasteurella haemolytica* A1 isolates were recovered from the left caudal lobe of goats from six treatment groups as follows: NC, 100%; PC, 40%; Ph 1-O, 17%; Ph 1-I, 0%, Ph 1-I-SC, 17%, CPS, 83%. The Ph 1 geometric mean group Ph 1 titers (CFU/ml) recovered from the right caudal lobe (challenge exposed) are as follows: 5 PC, $1.9\times10^2$; 6 NC, $2.2\times10^8$, 6 Ph 1-O, $4.3\times10^4$; 5 Ph 1-I, $4.4\times10^6$, 6 Ph 1-I-SC, $4.9\times10^6$; six CPS, $8.8\times10^5$.

Deaths After Challenge Exposure Prior to Termination of the Experiment

Six NC goats died on day 35, 3 CPS goats dies on day 35 and 2 on day 36, and 1 Ph 1-I-SC goat died on day 36. All deaths were due Ph 1 pneumonia induced by the challenge exposure.

Necropsy Results

Figure 7:
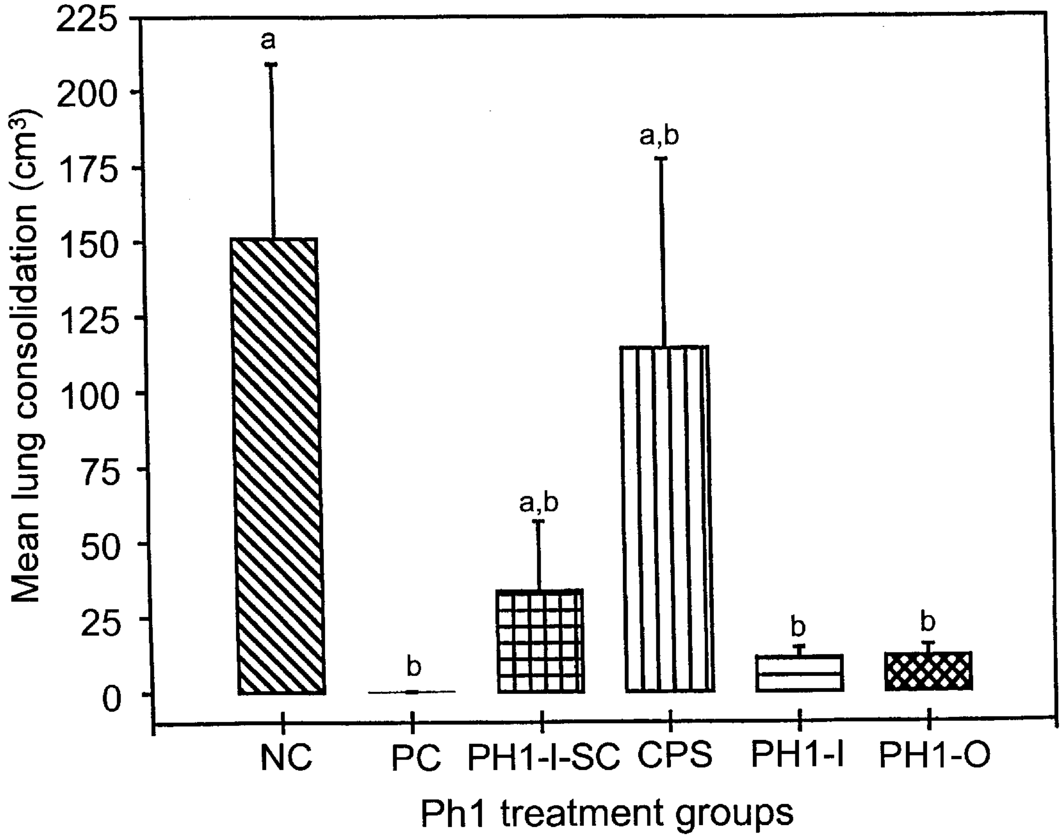
FIG. 7. Mean volume (cm$^3$) consolidated lung tissue of goats treated in Example 1. Means with different superscripts are significantly different among treatments ($P \leqq 0.05$).

There was a significant difference (P=0.04) among treatment groups in the mean volume of consolidation lung tissue (FIG. 7). The mean challenge-induced volume of consolidated right lung tissue, measured in ($cm^3$), by treatment groups are as follows: PC group, 0.06; NC group, 150.83; Ph 1-O group, 11.68; Ph 1-I group, 11.24; Ph 1-I-SC group, 33.47; and CPS group, 113.98 (P<0.042).

Conclusions

A significant increase in mean rectal temperature (FIG. 2) occurred in the PC group after the goats were injected with virulent live Ph 1. This was expected because pneumonia is induced at the injection site (Purdy et al., 1990, ibid). This bacterial multiplication at the injection site in the PC group induced solid immunity to a subsequent Ph 1 challenge exposure. However, if the titer of live bacteria injected is too high and the individual very susceptible, the pneumonia induced may overwhelm the goat and a fatal pneumonia may result before immunity can resolve the infection. This occurred in three positive controls two days after the first injection and is always a hazard when using highly virulent bacteria to induce immunity. However, the immunity induced in the survivors by such a procedure is usually of the most solid nature possible. This immunity is what we use to compare with any vaccine induced immunity. There was a significant difference (FIG. 3) in the total WBC counts among the treatment groups on day 7, because of the high WBC counts (mean 23,780) of the PC goats. This might be expected in every experiment, however significant differences in total WBC counts between treatment groups occur infrequently in our experience.

All treatment groups decreased in anticytotoxic antibody titers from day −21 to 0. This indicated a depleting passive anticytotoxin antibody titer. The PC group was the only group to make active anticytotoxin antibody (FIG. 4) after two injections of live Ph 1. It took 21 days for this response to occur and it peaked on day 34. The absence of anticytotoxin antibody in the Ph 1-O, Ph 1-I and Ph 1-I-SC groups appeared to have no effect on protective immunity against challenge exposure. Protective immunity against a severe lung challenge exposure was afforded to the PC, Ph 1-O, and Ph 1-I groups based on the small mean volume of consolidated lung tissue (FIG. 7; P=0.04) when compared to the NC and CPS groups. The Ph 1-I-SC group was partially protected by the same criteria, however one goat died due to the challenge exposure. Surviving goats which remained alive 4 days after a severe challenge exposure is another determination of protective immunity. All six of the NC goats died on day 35 and five out of six CPS goats died by day 36. These two groups were not protected from the Ph 1 challenge exposure.

EXAMPLE 2

A second trial was conducted to demonstrate the effectiveness of UV-killed *P. haemolytica* administered with polyacrylate microparticles (PA) as a vaccine for subcutaneous injection.

Fifty-one weanling goats were obtained from the same ranch and handled as described in Example 1. Live Ph 1 vaccine and UV-killed Ph 1 vaccine were prepared as described in Example 1.

Polyacrylate beads were prepared from DRYTECH Aqueous Fluid Absorbent 532 (the sodium salt of a cross-linked polypropenoic acid polymer, Dow Chemical Company, Midland, Mich.). DRYTECH 532 was ground for 48 hours using a roller mill (Model 753 RM, Norton Industries, Akron, Ohio) and 200 steel bearings and then sifted through a 200 mesh screen to obtain particles in the 3–4 $\mu$m range as described by Dr. J. McGrath (Personal Communication).

Experimental Design

The goats were randomly allotted to eight treatment groups as follows: 1) positive control group (PC1, n=9) receiving $10^5$ cfu of live Ph 1 transthoracicly twice, 2) a positive control (PC2, n=6) receiving $10^{10}$ live Ph 1 delivered to the respiratory tree by aerosolization (twice), 3) a negative control group (NC, n=6), 4) principals receiving $10^{10}$ UV-killed Ph 1 delivered transthoracicly (twice) to the lungs (PR1, n=6), 5) principals receiving $10^{10}$ cfu of UV-killed Ph 1 delivered subcutaneously (twice) (PR2, n=6), 6) principals receiving $10^{10}$ cfu of UV-killed Ph 1 delivered subcutaneously (PR3, n=6), (one injection), 7) principals receiving $10^{10}$ cfu of UV-killed Ph 1 delivered (twice) to the respiratory tree of goats by aerosolization (PR4, n=6), and finally 8) principals receiving $10^8$ cfu of UV-killed Ph A1 delivered by aerosolization (twice) to the respiratory tree of goats (PR5, n=6). All of the above groups received the PA beads in the vaccine injection. One gram of dried PA beads were used per aerosolization. One-tenth gram of liquid PA beads were used for each injection. The negative controls each received only sterile PA beads (0.5 ml in a saline slurry). The injections were given on day 0 and day 21 of the experiment.

Transthoracic, Aerosolization, and Subcutaneous Injection

The goats were tranquilized 15 min prior to the transthoracic injection of the appropriate PA bead preparation into the caudal lobe of the right lung, 2.5 cm caudal to the medium lobe. 0.5 ml of the PA bead slurry was injected at each treatment. Twenty-one days later, a second injection (the same preparation as the first) was performed as described above. Subcutaneous injections were done in thigh muscle tissue. Aerosolizations were performed using a Devilbliss powder insulfalator (HRI-8160-000119, The Devilbliss Co., Somerset, Pa.) to spray the PA bead—UV killed vaccine down the trachea of the goats. Forty-one days after injection of the appropriate PA bead preparation, controls and principals were challenged by injection of $1\times10^8$ cfu of live Ph A1 in 1 ml of physiological saline in the right lung. The injection technique used in the challenge exposure was the same as that described for day 0 transthoracic injection of PA beads. Goats were sacrificed on day 45.

Indirect Hemagglutination (IHA) Assay for Anti-Ph 1 Antibody

Figure 8A:
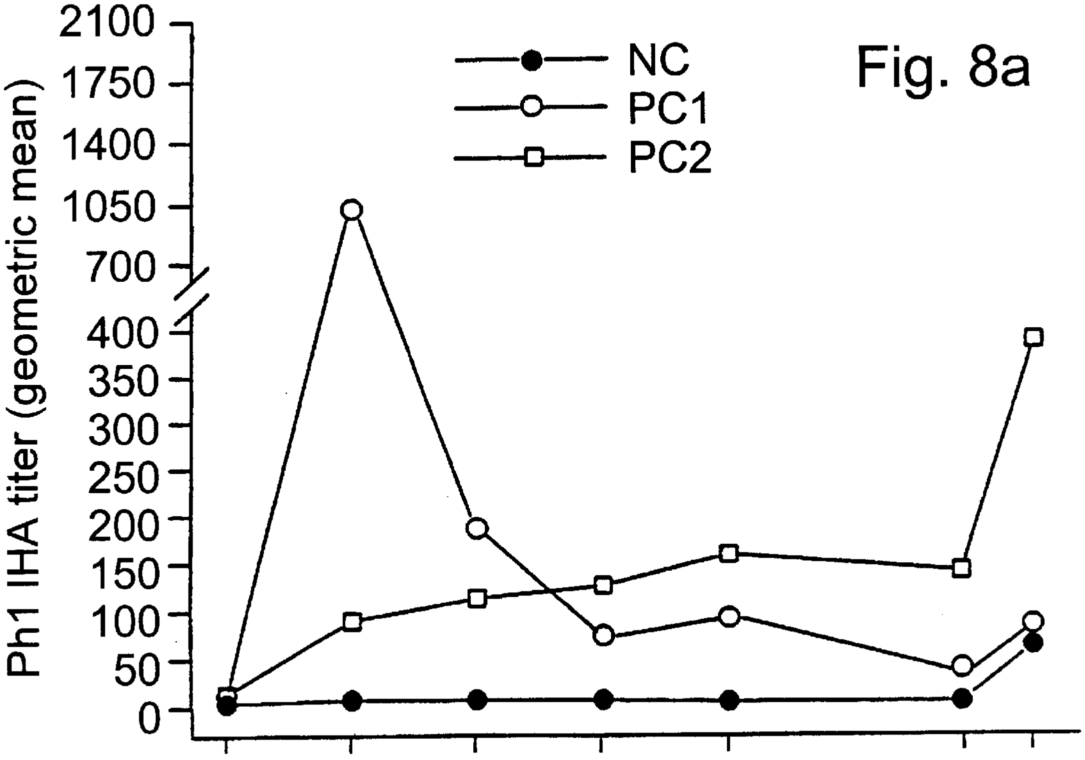
FIGS. 8(*a*) and (*b*). Comparison of *P. haemolytica* A1 indirect hemagglutination antibody titers of goats treated in Example 2.
Figure 8B:
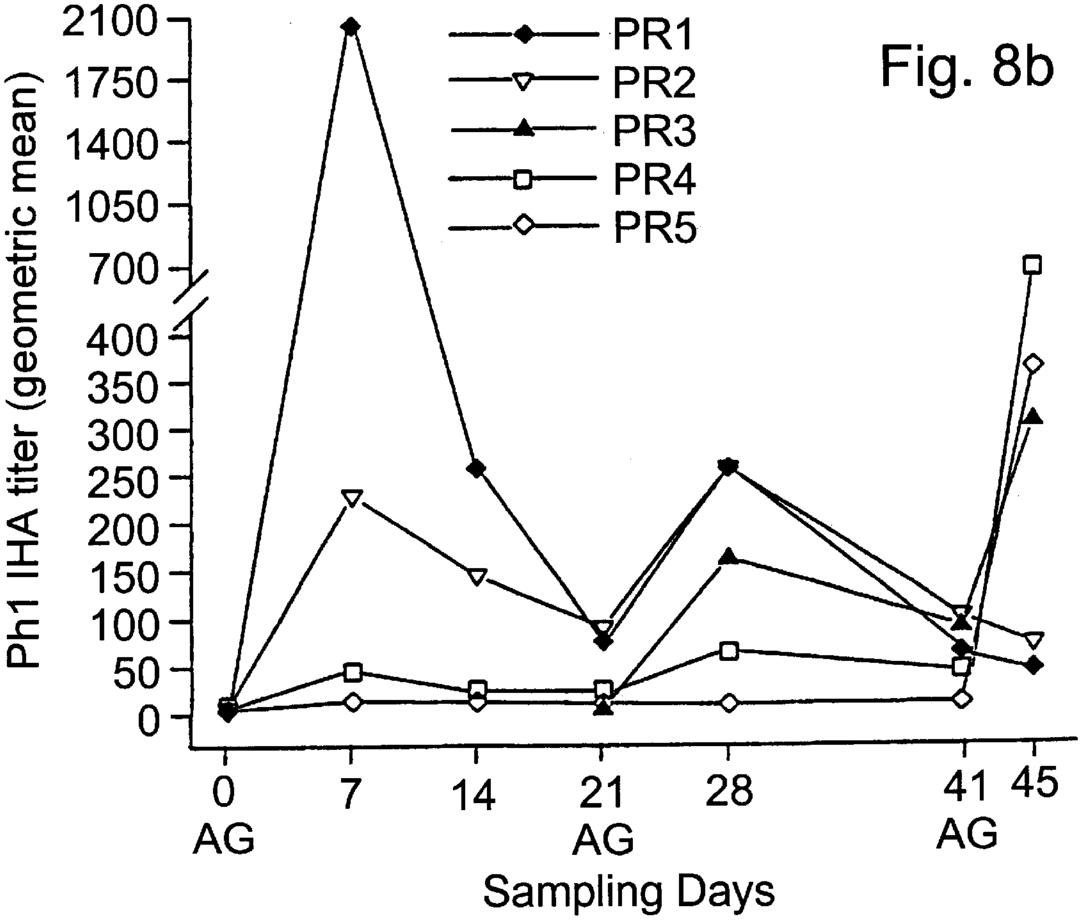

The Ph 1 IHA geometric mean titers of controls and principals (FIG. 8) were compared. IHA titers increased dramatically following the first injection of live Ph 1 (PC1) and UV-killed Ph 1 into the lungs (PR 1). The next best response was against the injection of $10^{10}$ cfu of UV-killed Ph 1 subcutaneously (PR2). All other injections demonstrated lower IHA responses following the first injection. Increases in the IHA titer were seen in PC2, and all of the principal groups (PR1, PR2, PR3, PR4)) except for PR5. There was essentially no Ab response in the negative control (NC) and $10^8$ cfu of UV-killed Ph 1 delivered to the respiratory tree by aerosolization. UV-killed Ph 1 plus PA beads delivered to the respiratory tree by aerosolization (PR4 and PR5) did not appear to induce a good anti-Ph 1 response. However, there was a better antibody response to PR4 than PR5 which had 100 fold-less UV-killed Ph A1.

Gross Pulmonary Lesions

Figure 9:
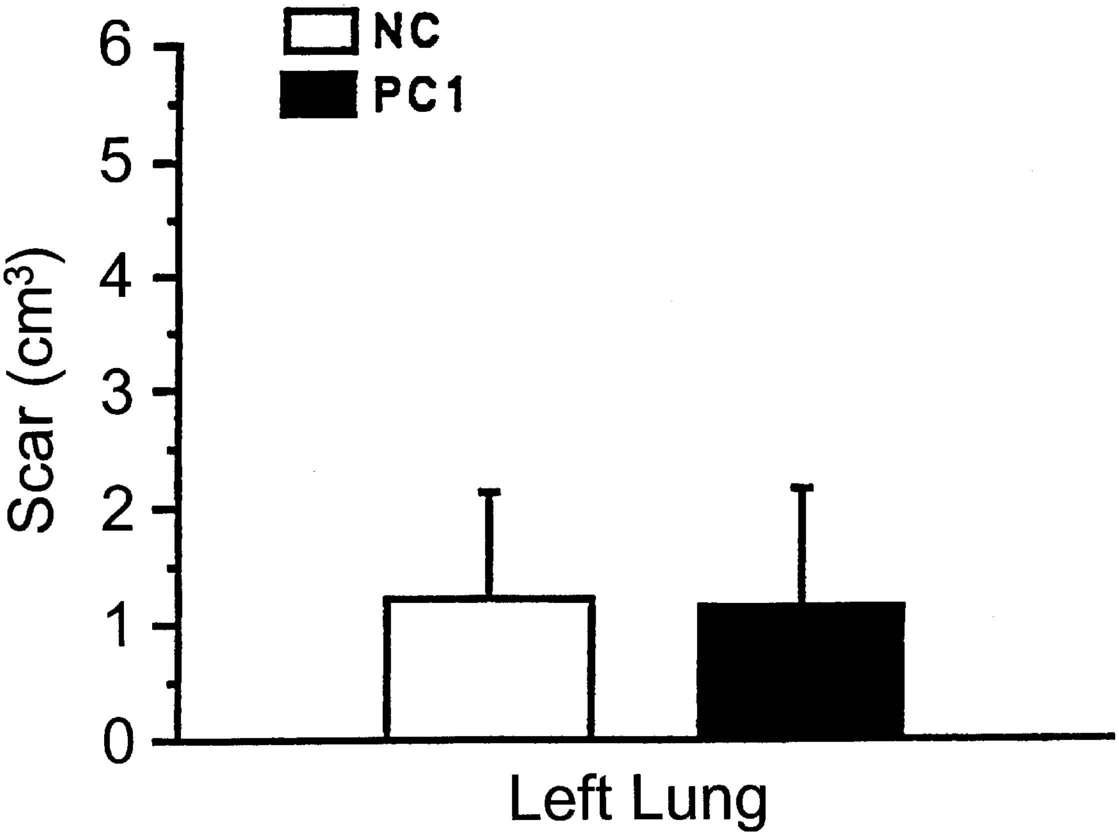
FIG. 9. Scar size in cm$^3$ at the vaccination site (left lung) following necropsy in Example 2.

There was essentially no scarring at the vaccination site (left lung) as a result of the negative control (NC) and the positive control group 1 (PC1) (FIG. 9). This demonstrated that the PA beads themselves caused little if any pathology. We were often able to see the PA beads in the lungs upon necropsy, but we never saw the PA beads in the subcutaneous tissues as a result of our injecting them at this location. This indicated that the beads were most probably draining to the regional lymph nodes and this may have been one of the reasons why this vaccination site provides such excellent protection (see FIG. 10).

Gross pathologic lesions consisted of pleural adhesions (small consolidated areas at the needle injection site) when Ph 1 impregnated beads given on day 0 and day 21 leaked from the injected lung of positive control goats. Large consolidated areas were observed 4 days after Ph 1 transthoracic challenge exposure in the right lung of all negative controls (NC) but only small areas of consolidation were observed into the positive controls (PC1 and PC2) (FIG. 9). The negative controls (NC) had consolidated lesion sizes of an average of 231 $cm^3$. The positive controls (PC1 and PC2) had lesion sizes of 1.72 and 2.02 $cm^3$, respectively. The animals that received $10^{10}$ UV-killed Ph 1 plus PA beads injected into the lungs transthoracicly (PR1) as the vaccine had consolidated lesions that averaged 2.83 $cm^3$. Animals that received $10^{10}$ UV-killed Ph 1 plus PA beads (2×) (PR2) injected subcutaneously had consolidated lesions that averaged 3.82 $cm^3$, a 60 fold reduction as compared to the negative controls. Animals that were injected with the same vaccine at the same site, but were only injected once (PR3) had consolidated lesions that averaged 157.99 $cm^3$, indicating that the vaccine containing $10^{10}$ UV-killed Ph A1 plus PA heads given subcutaneously, should preferably be given twice for maximum effectiveness. None of the other vaccines offered significant protection when compared to the negative controls.

Anticytotoxin Titers and Temperatures by Treatment Group

As expected, only positive control animals (those injected or aerosolized with live Ph 1) demonstrated any anticytotoxin antibody titers. The PC 1 group, which received live Ph 1 ($10^5$ cfu transthoracicly in the lungs) had an average anticytotoxin titer of approximately 110 at day 45. The PC 2 group, which received $10^{10}$ cfu of live Ph 1 delivered to the respiratory tree by aerosolization had an average titer of approximately 50. None of the animals receiving UV-killed Ph 1 in any form, produced any anticytoxin antibody. This is undoubtedly because UV-killed Ph 1 vaccine contains only trace amounts of cytotoxin.

As expected, the temperatures increased significantly in animals receiving the lung injection of live Ph 1 (PC1), at day 0. Surprisingly, the animals receiving live Ph 1 by aerosolization to their respiratory tree showed no elevation in temperature. Also animals receiving UV-killed Ph 1 by injection into the lungs (PR1) and those receiving UV-killed Ph 1 subcutaneously (PR2 and PR3) also showed elevated temperatures. These trends continued following the second antigen injection at day 21. The average temperatures of all groups elevated significantly on day 42 following the live transthoracic challenge of $1\times10^8$ Ph 1 into the right lung.

Figure 10A:
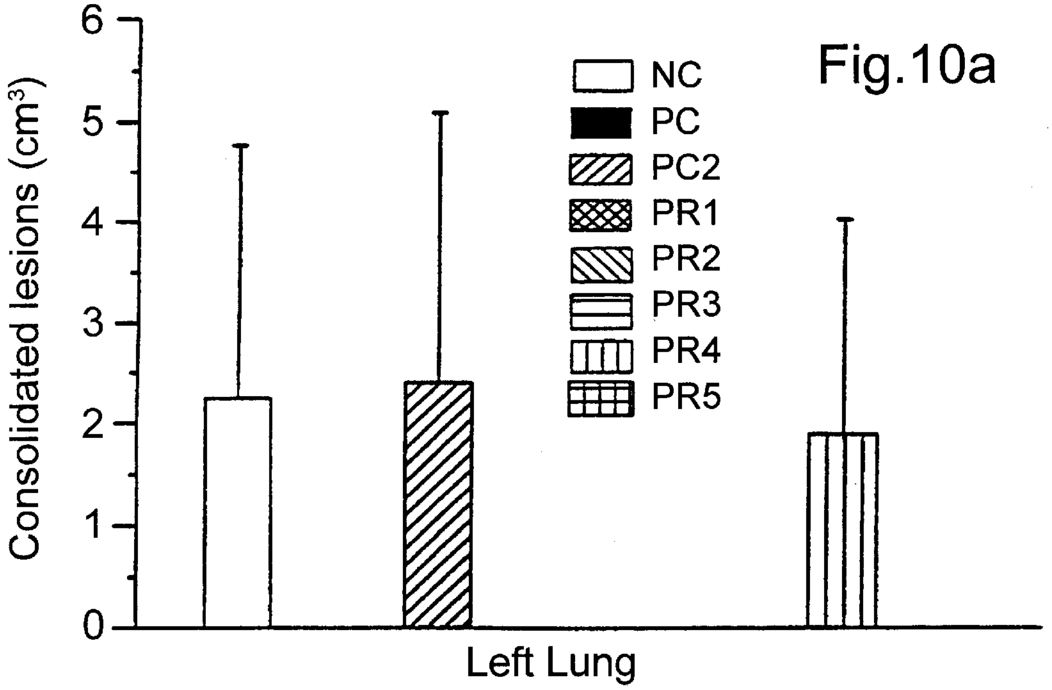
FIGS. 10(*a*) and (*b*). Comparison of mean area of pneumonic consolidation (right lung) between principals and controls 4 days after transthoracic challenge exposure with live Ph A1 ($1 \times 10^8$ cfu). Left lung consolidation represents the consolidation at the vaccination site where the vaccine was introduced into the lungs. Group legends are the same as described in FIG. 8.
Figure 10B:
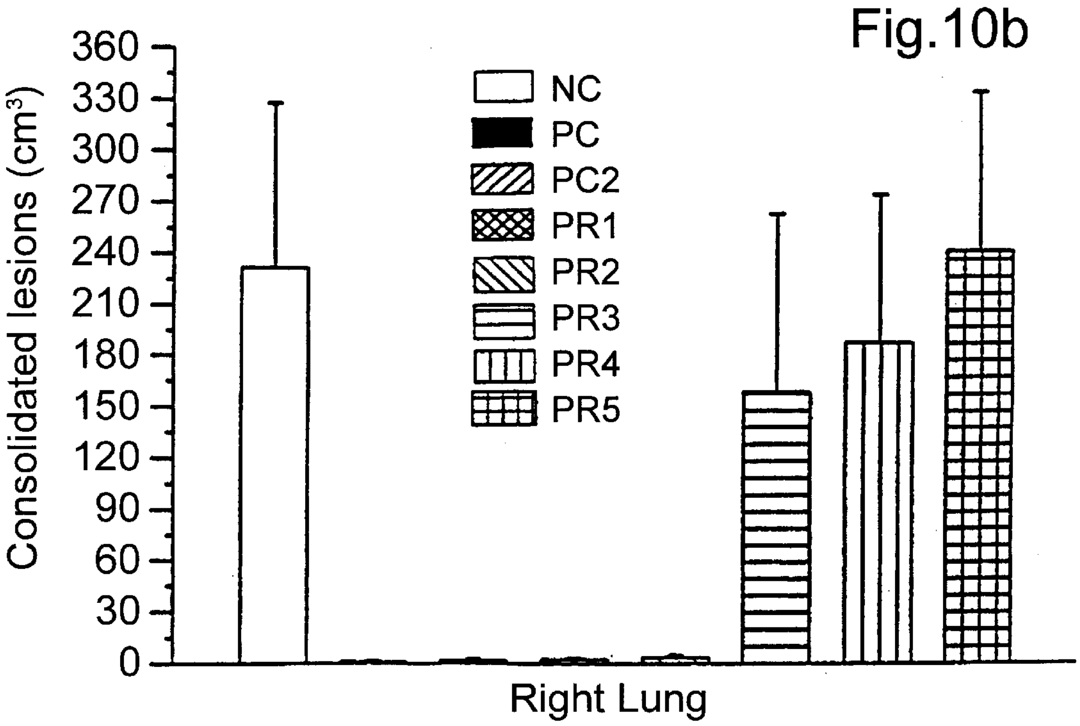

The results supra indicate that the vaccine of the invention offers protection at a level comparable to an actual Ph 1 pneumonia. FIG. 10 clearly shows that the vaccine (PR2) protected goats against $1\times10^8$ cfu of live Ph 1 delivered transthoracicly (average consolidated lesion size 3.82 $cm^3$) nearly as well as did an actual Ph 1 lung infection (PC1) where the average consolidated lesion size was 1.72 $cm^3$.

It is understood that the foregoing detailed description is given merely by way of illustration and that modifications and variations may be made therein without departing from the spirit and scope of the invention.

We claim:

1. A composition comprising a dosage of whole killed cells of *Pasteurella haemolytica* effective to immunize an animal against *Pasteurella haemolytica* in combination with a pharmaceutically acceptable carrier and an adjuvant, wherein said killed *Pasteurella haemolytica* are produced by a process comprising irradiating viable cells of *Pasteurella haemolytica* with ultraviolet light for a sufficient period of time to kill 100% of said cells.

2. The composition of claim 1 wherein said killed *Pasteurella haemolytica* are impregnated in a microparticle or microcapsule of a biocompatible matrix material.

3. The composition of claim 2 wherein said matrix material is selected from the group consisting of agar and polyacrylate.

4. The composition of claim 1 further comprising microparticles of a biocompatible matrix material.

5. The composition of claim 4 wherein said microparticles are selected from the group consisting of agar and polyacrylate.

6. The composition of claim 1 wherein said adjuvant is selected from the group consisting of Freund's incomplete adjuvant, Freund's complete adjuvant, and oil.

7. The composition of claim 1 wherein said carrier comprises oil.

8. The composition of claim 1 wherein said viable cells of *Pasteurella haemolytica* are A biotype.

9. The composition of claim 8 wherein said viable cells of *Pasteurella haemolytica* are A biotype, 1 serotype.

10. The composition of claim 1 containing at least about $10^6$ of said killed cells *Pasteurella haemolytica.*

11. The composition of claim 10 containing at least about $10^8$ of said killed cells *Pasteurella haemolytica.*

12. A method of protecting an animal against infection by *Pasteurella haemolytica* comprising administering the composition of claim 1 to said animal.

13. The method of claim 12 wherein said animal is selected from the group consisting of goats, sheep and bovine.

14. A composition comprising a dosage of whole killed cells of *Pasteurella haemolytica* effective to immunize an animal against *Pasteurella haemolytica* in combination with a pharmaceutically acceptable carrier, wherein said killed *Pasteurella haemolytica* are produced by a process comprising irradiating viable cells of *Pasteurella haemolytica* with ultraviolet light for a sufficient period of time to kill 100% of said cells, and further wherein said killed *Pasteurella haemolytica* are impregnated in a microparticle or microcapsule of a biocompatible matrix material.

15. The composition of claim 14 wherein said matrix material is selected from the group consisting of agar and polyacrylate.

16. A composition comprising a dosage of whole killed cells of *Pasteurella haemolytica* effective to immunize an animal against *Pasteurella haemolytica* in combination with a pharmaceutically acceptable carrier and microparticles of a biocompatible matrix material, wherein said killed *Pasteurella haemolytica* are produced by a process comprising irradiating viable cells of *Pasteurella haemolytica* with ultraviolet light for a sufficient period of time to kill 100% of said cells.

17. The composition of claim 16 wherein said microparticles are selected from the group consisting of agar and polyacrylate.

18. A composition comprising a dosage of whole killed cells of *Pasteurella haemolytica* effective to immunize an animal against *Pasteurella haemolytica* in combination with a pharmaceutically acceptable carrier, wherein said killed *Pasteurella haemolytica* are produced by a process comprising irradiating viable cells of *Pasteurella haemolytica* with ultraviolet light for a sufficient period of time to kill 100% of said cells, and further wherein said carrier comprises oil.

* * * * *